(12) United States Patent
Hsu et al.

(10) Patent No.: US 8,961,971 B2
(45) Date of Patent: Feb. 24, 2015

(54) BISPECIFIC T-CELL ACTIVATOR ANTIBODY

(71) Applicants: Development Center for Biotechnology, New Taipei (TW); DCB-USA LLC, Wilmington, New Castle, DE (US)

(72) Inventors: Yu-Shen Hsu, New Taipei (TW); Show-Shan Sheu, New Taipei (TW); Ming-I Chang, New Taipei (TW); Ming-Chuan Chang, New Taipei (TW); Ta-Tung Yuan, New Taipei (TW)

(73) Assignees: Development Center for Biotechnology, New Taipei (TW); DCB-USA LLC, Wilmington, New Castle, DE (US)

(*) Notice: Subject to any disclaimer, the term of this patent is extended or adjusted under 35 U.S.C. 154(b) by 0 days.

(21) Appl. No.: 13/720,573

(22) Filed: Dec. 19, 2012

(65) Prior Publication Data

US 2013/0165629 A1   Jun. 27, 2013

Related U.S. Application Data

(60) Provisional application No. 61/579,450, filed on Dec. 22, 2011.

(51) Int. Cl.
| | | |
|---|---|---|
| *A61K 39/00* | (2006.01) | |
| *A61K 39/395* | (2006.01) | |
| *A61K 38/00* | (2006.01) | |
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C12P 21/08* | (2006.01) | |
| *A61K 38/10* | (2006.01) | |
| *A61K 38/16* | (2006.01) | |
| *A61K 38/08* | (2006.01) | |
| *C07K 16/46* | (2006.01) | |
| *C07K 7/06* | (2006.01) | |
| *C07K 7/08* | (2006.01) | |
| *C07K 16/28* | (2006.01) | |

(52) U.S. Cl.
CPC ............. *C07K 16/468* (2013.01); *C07K 7/06* (2013.01); *C07K 7/08* (2013.01); *C07K 16/2809* (2013.01); *C07K 16/2887* (2013.01); *C07K 2317/53* (2013.01); *C07K 2317/622* (2013.01); *C07K 2317/64* (2013.01); *C07K 2317/732* (2013.01); *C07K 2317/74* (2013.01); *C07K 2317/94* (2013.01)
USPC .............. 424/136.1; 424/133.1; 424/138.1; 530/326; 530/328; 530/387.3; 530/387.7; 514/21.4; 514/21.5; 514/21.8

(58) Field of Classification Search
None
See application file for complete search history.

(56) References Cited

U.S. PATENT DOCUMENTS

| | | | |
|---|---|---|---|
| 6,896,885 B2* | 5/2005 | Hanna | 424/156.1 |
| 2008/0260738 A1 | 10/2008 | Moore et al. | |
| 2008/0299120 A1 | 12/2008 | Miller et al. | |
| 2009/0117104 A1* | 5/2009 | Baker et al. | 424/133.1 |
| 2009/0186020 A1* | 7/2009 | Cunningham et al. | 424/133.1 |
| 2011/0104112 A1 | 5/2011 | Morrison et al. | |
| 2011/0243966 A1 | 10/2011 | Farrington et al. | |
| 2013/0129723 A1* | 5/2013 | Blankenship et al. | 424/134.1 |

OTHER PUBLICATIONS

U.S. Appl. No. 13/728,839, filed Dec. 2012, Hsu et al.*
International Search Report and Written Opinion mailed Apr. 22, 2013, by the Korean Intellectual Property Office in related International Application No. PCT/US2012/070432 (10 pages).
International Preliminary Report on Patentability (IPRP) issued Jun. 24, 2014, in corresponding International Application No. PCT/US2012/070432 (5 pages).

* cited by examiner

*Primary Examiner* — James H Alstrum Acevedo
*Assistant Examiner* — Thea D'Ambrosio
(74) *Attorney, Agent, or Firm* — Osha Liang LLP

(57) ABSTRACT

This invention relates to bispecific antibodies having combinations of linker and hinge sequences to create linker-hinge interface domains with biological significance. Such linker-hinge interface domains covalently join two molecules, maintain the biological activities of linked molecules (target binding), stabilize the biological characteristics of new molecule (solubility and 4° C. stability), maintain the chemical, biochemical and physical properties (cytotoxicity) of the linked molecules, and modulate the biological characteristics of the linked molecules (activating T-lymphocytes without significant sign of proliferations). Both linker (GGGGS) and hinge (CPPCP) sequences are required to establish functional linker-hinge interface domains as deletion of any of the component resulted in significant lost of T-lymphocyte mediated activity.

14 Claims, 14 Drawing Sheets

Anti-CD20/ScFv-IgG/Fc-LHD-anti-CD3/ScFv
(ScFv-IgG BsAb with LHD)

Anti-CD20-IgG-LHD-anti-CD3/ScFv
(IgG-FL BsAb with LHD)

Anti-CD20/ScFv-IgG/Fc-LHD/ΔGGGGS-anti-CD3/ScFv
(ScFv-IgGΔL BsAb)

Anti-CD20-IgG-LHD/ΔCPPCP-anti-CD3/ScFv
(IgG-FLΔH BsAb)

Anti-CD3/ScFv-IgG/Fc-LHD-anti-CD20/ScFv
(N-terminal TAD BsAb)

The binding affinity decreased significantly for IgG-FLΔH construct

Binding to CD3 by IgG-FL is not effected by LHD formats

IgG-FLΔH construct showed significant aggregation following purification

1. IgG-FLΔH: Pellet
2. IgG-FLΔH: supernatant
3. Anti-CD20 mAb
4. Prestain markers IgG-FL showed good stability after 3 months storage in 4°C LHD fusion ScFV-IgG BsAb mediated cytotoxicity against tumor LHD fusion IgG-FL BsAb mediated cytotoxicity against tumor LHD fusion IgG-FL BsAb mediated cytotoxicity against tumor IgG-FL induces mild proliferation on PBMC

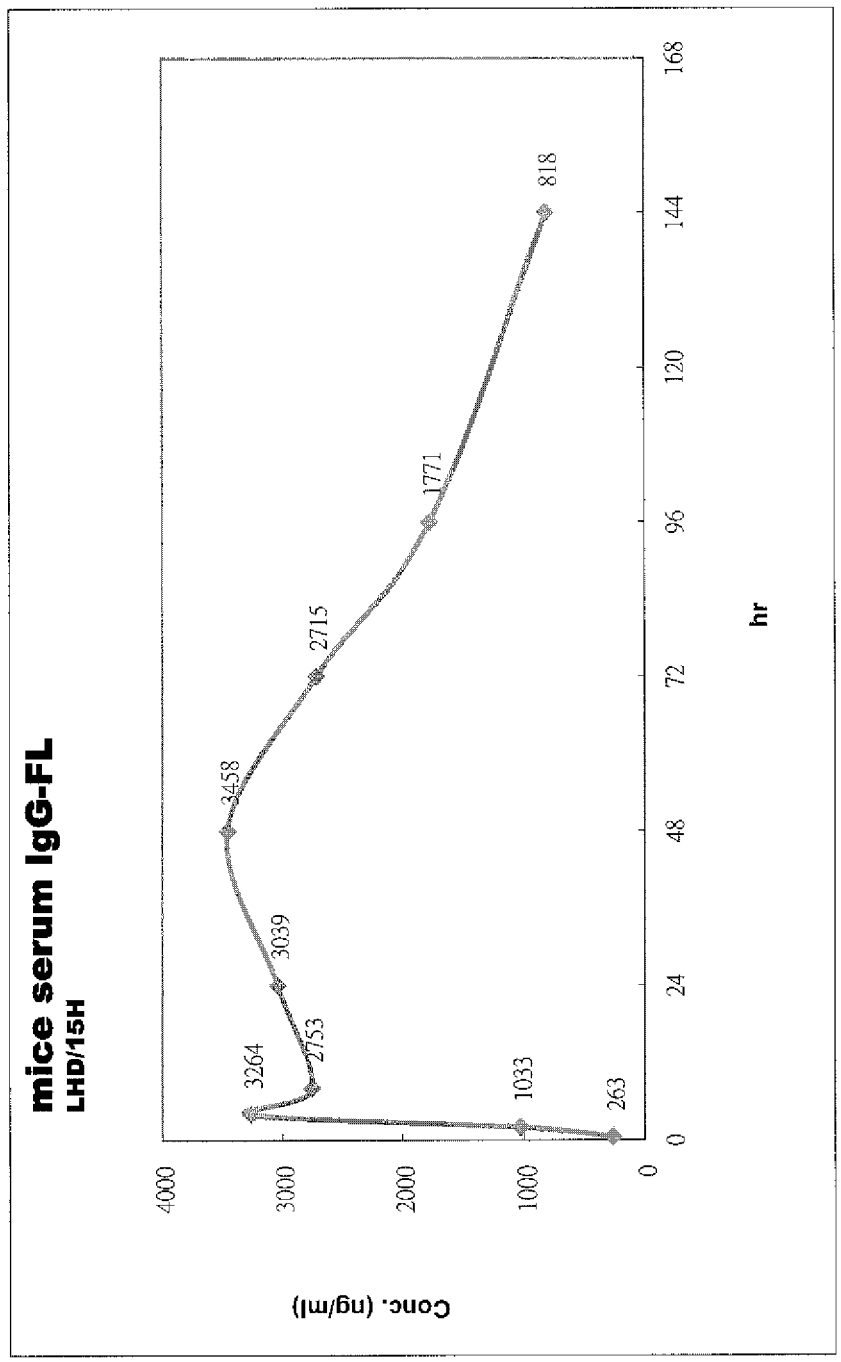
Figure 7: PK analysis on LHD fused BsAb

SEQUENCE LISTING

```
<160> NUMBER OF SEQ ID NOS: 9

<210> SEQ ID NO 1
<211> LENGTH: 20
<212> TYPE: PRT
<213> ORGANISM: Artificial
<220> FEATURE:
<223> OTHER INFORMATION: linker

<400> SEQUENCE: 1

Gly Gly Gly Gly Ser Gly Gly Gly Gly Ser Gly Gly Gly Gly Ser Cys
1               5                   10                  15

Pro Pro Cys Pro
```

20

<210> SEQ ID NO 2
<211> LENGTH: 15
<212> TYPE: PRT
<213> ORGANISM: Artificial
<220> FEATURE:
<223> OTHER INFORMATION: Linker

<400> SEQUENCE: 2

Gly Gly Gly Gly Ser Gly Gly Gly Ser Cys Pro Pro Cys Pro
1               5                   10                  15

<210> SEQ ID NO 3
<211> LENGTH: 10
<212> TYPE: PRT
<213> ORGANISM: Artificial
<220> FEATURE:
<223> OTHER INFORMATION: Linker

<400> SEQUENCE: 3

Gly Gly Gly Gly Ser Cys Pro Pro Cys Pro
1               5                   10

<210> SEQ ID NO 4
<211> LENGTH: 20
<212> TYPE: PRT
<213> ORGANISM: Artificial
<220> FEATURE:
<223> OTHER INFORMATION: Linker

<400> SEQUENCE: 4

Gly Gly Gly Gly Ser Gly Gly Gly Ser Cys Pro Pro Cys Pro Gly
1               5                   10                  15

Gly Gly Gly Ser
            20

<210> SEQ ID NO 5
<211> LENGTH: 20
<212> TYPE: PRT
<213> ORGANISM: Artificial
<220> FEATURE:
<223> OTHER INFORMATION: Linker

<400> SEQUENCE: 5

Gly Gly Gly Gly Ser Cys Pro Pro Cys Pro Gly Gly Gly Ser Gly
1               5                   10                  15

Gly Gly Gly Ser
            20

<210> SEQ ID NO 6
<211> LENGTH: 15
<212> TYPE: PRT
<213> ORGANISM: Artificial
<220> FEATURE:
<223> OTHER INFORMATION: Linker

<400> SEQUENCE: 6

Gly Gly Gly Gly Ser Cys Pro Pro Cys Pro Gly Gly Gly Gly Ser
1               5                   10                  15

<210> SEQ ID NO 7
<211> LENGTH: 20
<212> TYPE: PRT
<213> ORGANISM: artificial
<220> FEATURE:

```
<223> OTHER INFORMATION: Linker

<400> SEQUENCE: 7

Gly Gly Gly Gly Ser Gly Gly Gly Gly Ser Gly Gly Gly Gly Ser Gly
1               5                   10                  15

Gly Gly Gly Ser
            20

<210> SEQ ID NO 8
<211> LENGTH: 5
<212> TYPE: PRT
<213> ORGANISM: Artificial
<220> FEATURE:
<223> OTHER INFORMATION: Hinge

<400> SEQUENCE: 8

Cys Pro Pro Cys Pro
1               5

<210> SEQ ID NO 9
<211> LENGTH: 5
<212> TYPE: PRT
<213> ORGANISM: Artificial
<220> FEATURE:
<223> OTHER INFORMATION: Linker

<400> SEQUENCE: 9

Gly Gly Gly Gly Ser
1               5
```

BISPECIFIC T-CELL ACTIVATOR ANTIBODY

CROSS REFERENCE TO RELATED APPLICATION

This claims the benefits of the Provisional Application No. 61/579,450, filed on Dec. 22, 2011, the disclosure of which is incorporated by reference in its entirety.

FIELD OF THE INVENTION

This invention relates to methods for preparing bispecific or multi-specific biomolecules, such as bispecific antibodies, and products thereof. Particularly, the invention relates to novel cross-linkers for cross-linking molecules and methods of using the same.

BACKGROUND OF THE INVENTION

Combining biological molecules having different functions may lead to new molecules with desired or improved properties. For example, the combined molecules may have dual functions and may have improved stabilities. A common approach to combining biomolecules is to cross-link these molecules with chemical linking agents. However, the biological activities of combined molecules are not always preserved when chemically cross-linked. Therefore, there remains a need for better methods for cross-linking biomolecules.

SUMMARY OF THE INVENTION

This invention relates to methods for preparing bispecific or multi-specific biomolecules, such as bispecific antibodies (BsAbs), and products thus made. Particularly, the invention relates to novel linker-hinge domain for linking biomolecules and methods of using the same.

One aspect of the invention relates to protein domains that are referred to as "linker-hinge domains" (LHDs). An LHD in accordance with one embodiment of the invention includes a linker sequence and a hinge sequence, wherein the linker sequence comprises glycine-glycine-glycine-glycine-serine (GGGGS; SEQ ID NO: 9), and the hinge sequence comprises cysteine-proline-proline-cysteine-proline (CPPCP; SEQ ID NO: 8). The LHD may include two or more linker sequences. Examples of the LHD domain may include the sequences of SEQ ID NO: 1, SEQ ID NO: 2, SEQ ID NO: 3, SEQ ID NO: 4, SEQ ID NO: 5, or SEQ ID NO: 6

One aspect of the invention relates to proteins having the above-described LHD domains. A protein in accordance with one embodiment of the invention may further include an N-terminal moiety fused to the N-terminus of the protein domain via a peptide bond and/or a C-terminal moiety fused to the C-terminus to the protein domain via a peptide bond. The N-terminal moiety and the C-terminal moiety each may be independently a peptide, a full-length immunoglobulin, or a single-chain variable region fragment (ScFv) of an antibody. For example, one of the N-terminal moiety and the C-terminal moiety may include a T-lymphocyte activating domain that comprises an anti-CD3 antibody or a single-chain variable region fragment (ScFv) of the anti-CD3 antibody, while the other of the N-terminal moiety and the C-terminal moiety may include a tumor recognition domain that comprises an anti-CD20 antibody or a single-chain variable region fragment (ScFv) of the anti-CD20 antibody. Alternatively, the N-terminal moiety comprises comprising an anti-tumor specific marker, an inflammatory disease marker, an autoimmune disease marker, or an allergy-related marker.

One aspect of the invention relates to biomolecules, each of which comprises a dimer of the above-described protein having disulfide linkages between the hinge sequences of the dimer. The biomolecule maintains a T-lymphocyte activation capability, or the biomolecule maintains an antibody to antigen binding capability. The biomolecules may have improved solubilities, stabilities, and pharmacokinetics.

Other aspects and advantages of the invention will be apparent from the following description and the appended claims.

BRIEF DESCRIPTION OF THE DRAWINGS

FIG. 7 shows pharmacokinetic (PK) analysis of LHD fused BsAb according to one embodiment of the invention.

DETAILED DESCRIPTION

Figure 1A:
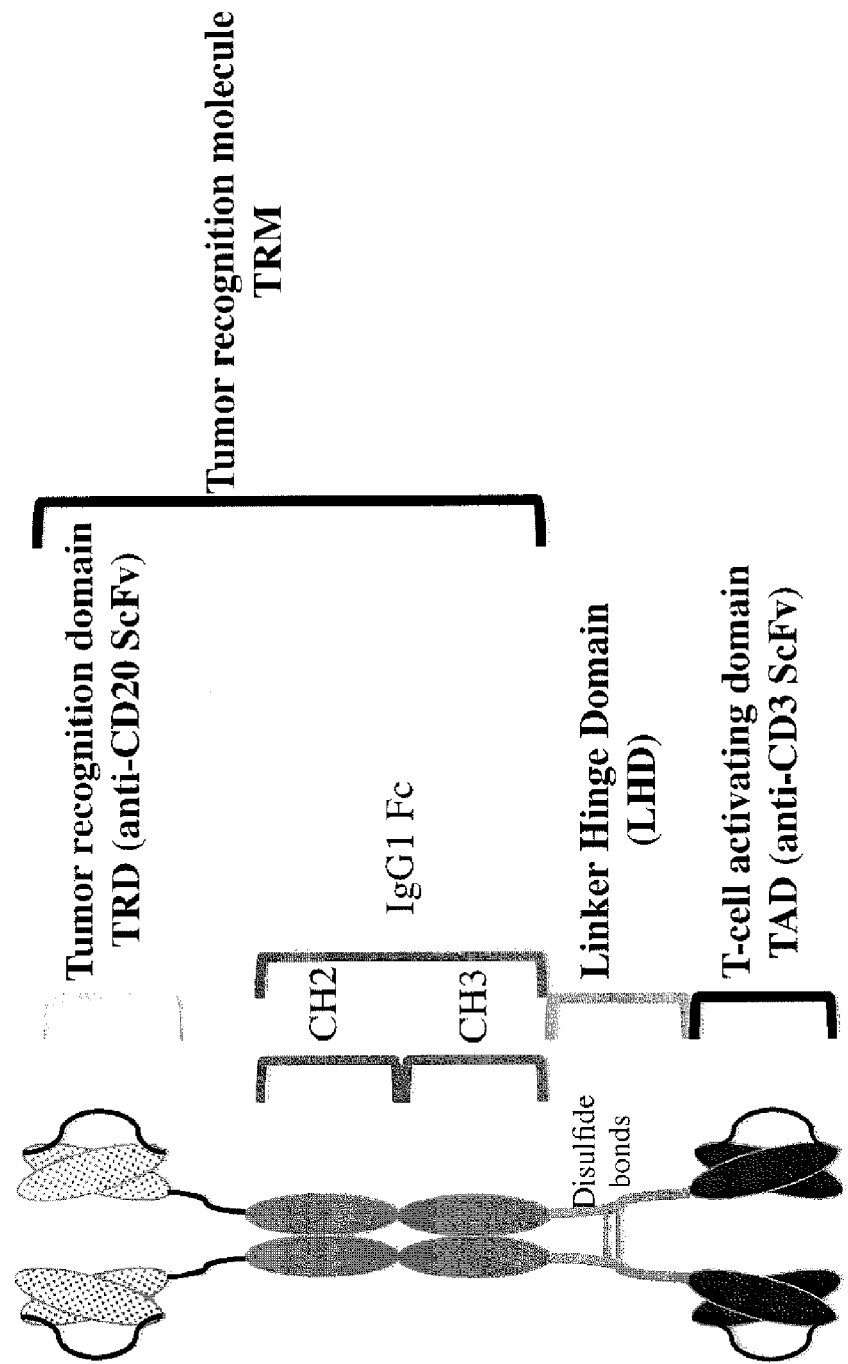
FIGS. 1A-1E show schematics illustrating constructs of various bispecific antibodies (BsAbs) in accordance with embodiments of the invention.

Embodiments of the invention relate to methods for preparing bispecific or multi-specific biomolecules, such as bispecific antibodies, and products thereof. Some embodiments of the invention relate to novel cross-linkers for cross-linking molecules and methods of using the same. A cross-linker of the invention may comprise a linker domain and a hinge domain. Therefore, these cross-linkers may be referred to as "linker-hinge domains" or LHDs.

In accordance with embodiments of the invention, a linker domain may have a sequence of glycine-glycine-glycine-glycine-serine (GGGS; SEQ ID NO:9), and a hinge domain may have a sequence of cysteine-proline-proline-cysteine-proline (CPPCP; SEQ ID NO:8). Some cross-linkers may comprise one or more linker sequences. The hinge sequences allow for disulfide bridge formations between dimers of molecules containing such sequences In accordance with embodiments of the invention, these LHDs may be used to construct bispecific or multi-specific biomolecules. The biomolecules may be antibodies, i.e., bispecific or multi-specific antibodies. A bispecific antibody may be referred to as "BsAb" in this description.

A bispecific antibody in accordance with embodiments of the invention may comprise an LHD linked to a constant region fragment (Fe) of an immunoglobulin (IgG) via a peptide bond—i.e., a fused protein of IgG-Fc-LHD. At the N-terminus and the C-terminus of this fusion protein, two specific ligand binding moieties may be attached to produce a bispecific biomolecule. A specific ligand binding moiety on the N-terminus or C-terminus of LHD-IgG Fc may be a protein or a peptide. Examples of such moieties may include a single-chain variable region of an antibody (referred to as "ScFv") or a peptide that binds a specific ligand (including an antigen).

Bispecific biomolecules of the invention may have an antibody-like structure and will be referred to as "bispecific antibodies" or BsAbs. The following will describe some examples to illustrate embodiments of the invention. While only a limited number of examples are described, one skilled in the art would appreciate that other modifications or variations of these examples are possible without departing from the scope of the invention.

Examples

Constructing CD20-Targeting, Bispecific Antibodies (BsAb with LHD)

To improve the biological functionalities of multi-specific molecules, bispecific antibodies (BsAb) comprising a linker-hinge interface domain (LHD) are constructed and tested for their functions. As used herein, a "linker-hinge" interface domain ("LHD") includes one or more glycine-glycine-glycine-glycine-serine (GGGGS or G$_4$S linker; SEQ ID NO:9) linker sequences and a single cysteine-proline-proline-cysteine-proline (CPPCP; SEQ ID NO:8 hinge) hinge sequence, were constructed. (Table 1)

TABLE 1

List of Linker-Hinge Domain Sequences

| Codes | LHD Sequences | SEQ ID No. |
|---|---|---|
| 15H | GGGGSGGGGSGGGGSCPPCP | 1 |
| 10H | GGGGSGGGGSCPPCP | 2 |
| 5H | GGGGSCPPCP | 3 |
| 10H5 | GGGGSGGGGSCPPCPGGGGS | 4 |
| 5H10 | GGGGSCPPCPGGGGSGGGGS | 5 |
| 5H5 | GGGGSCPPCPGGGGS | 6 |
| ΔH | GGGGSGGGGSGGGGSGGGGS | 7 |
| ΔL | CPPCP | 8 |

Embodiments of the invention use such LHDs to physically connect multiple functional biological molecules, including peptides and proteins. These linked biomolecules have one or more advantages, including maintaining the biological activities of linked molecules/domains, stabilizing the biological characteristics of new molecule, maintaining the chemical, biochemical and physical properties, modulating the biological characteristics, and etc.

To illustrate the beneficial roles of LHD in the construction of multi-specific molecules, several BsAb with LHD formats that recognize CD20 and CD3 as tumor marker and T-lymphocyte activating molecule, respectively, were constructed. These BsAb constructs, including anti-CD20/Sav-IgG/Fc-CH2-CH3-LHD-anti-CD3/ScFv (ScFv-IgG BsAb), anti-CD20 (Full mAb)-LHD-anti-CD3/ScFv (IgG-FL BsAb), and anti-CD20 (Full mAb)-LHD/ΔCPPCP-anti-CD3/ScFv (IgG-FLΔH), were constructed (FIGS. 1A-1E).

FIG. 1A illustrates an example of generating a bispecific antibody (BsAb) containing a tumor recognition domain (TRD), which comprises a single-chain variable fragment (ScFv) of an anti-CD20 monoclonal antibody (mAb), and a T-cell activating domain (TAD), which comprises a single-chain variable fragment (ScFv) of an anti-CD3 mAb. In this example, a tumor recognition molecule (TRM), abbreviated as ScFv-IgG, is constructed that comprises two parts: a tumor recognition domain (TRD) and an IgG constant heavy chain domain. The tumor recognition domain (TRD) comprises the ScFv of the anti-CD20 mAb. The IgG constant heavy chain domain comprises the CH2 and CH3 domains of an immunoglobulin G1 constant fragment (IgG1 Fc).

Then, the TRM is linked to an LHD (linker hinge domain), which comprises an LHD sequence of any of the LHD sequences listed in Table 1 (except SEQ No. 7). The LHD is covalently fused to the C-terminus of the CH3 domain of TRM. Finally, the T-lymphocyte activating domain (TAD), a.k.a. single chain anti-CD3 monoclonal antibody domain, is fused to the C-terminus of LHD. In other words, this recombinant protein comprises (from the N-terminus to the C-terminus): TRD (anti-CD20 ScFv), IgG1 Fc, LHD, and TAD (anti-CD3 ScFv).

As in a regular antibody, the biologically active form of this ScFv-IgG bispecific antibody (BsAb) will form a homodimer. The CPPCP sequence (SEQ ID NO:8) in the LHD domain of a monomeric ScFv-IgG BsAb could form disulfide linkages with the CPPCP sequence (SEQ ID NO:8) in the other LHD domain of the other monomeric ScFv-IgG following dimerization, as shown in FIG. 1A. The resultant molecule is an antibody-like molecule having two different variable domains on both ends (the C-terminal end and the N-terminal end) of the constant chain (i.e., IgG1 Fc). Thus, the resultant molecule may be referred to as a bispecific antibody (BsAb).

Figure 1B:
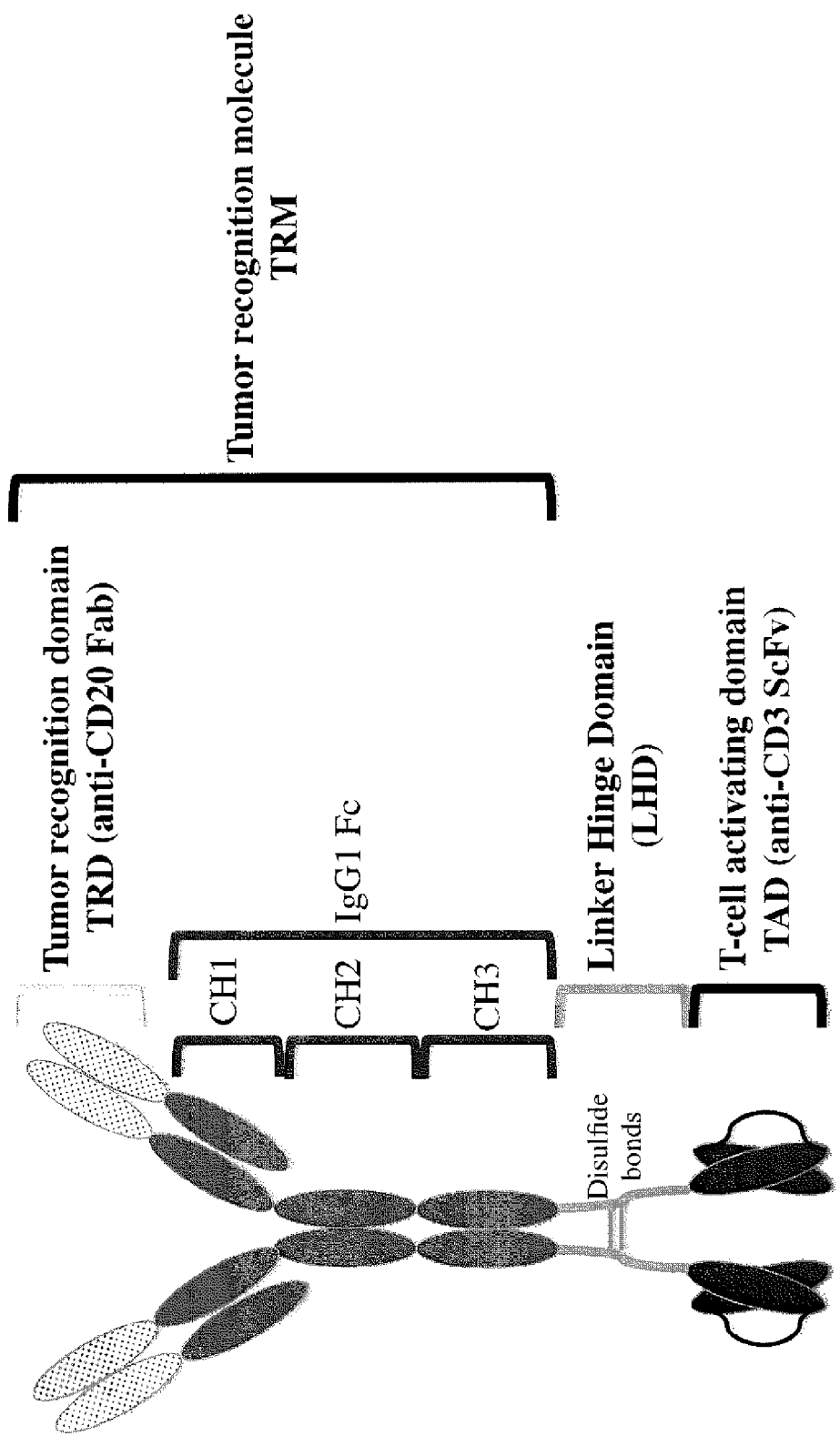

FIG. 1B illustrates another approach to forming a bispecific antibody (BsAb), having the same bi-specificities (i.e., anti-CD20 and anti-CD3) as those shown in FIG. 1A. This BsAb is similar to the one shown in FIG. 1A, except that a full-length anti-CD20 mAb is used, instead of a single-chain anti-CD20 antibody, for the TRM. The full length mAb includes a full length IgG1 constant heavy chain (IgG1 Fc), i.e., the heavy chain constant domain includes CH1, CH2, and CH3 domains.

As in the ScFv-IgG BsAb described above (FIG. 1A), an LHD is fused to the C-terminus of the TRM (i.e., the full-length anti-CD20 mAb)—i.e., fused to the C terminus of CH3 domain of the TRM. The LHD sequences may be any sequence in Table 1 except SEQ No. 7. Then, the TAD (i.e., anti-CD3 ScFv) is fused to the C terminus of the LHD sequence. As in the ScFv-IgG BsAb shown in FIG. IA, this construct will form a dimer. The CPPCP sequence in the LHD of a monomeric IgG-FL BsAb could form disulfide linkages to the LHD of another monomeric IgG-FL upon dimerization, as shown in 1B. The bi-specificities of this molecule would be the same as those of the one shown in FIG. 1A.

Figure 1C:
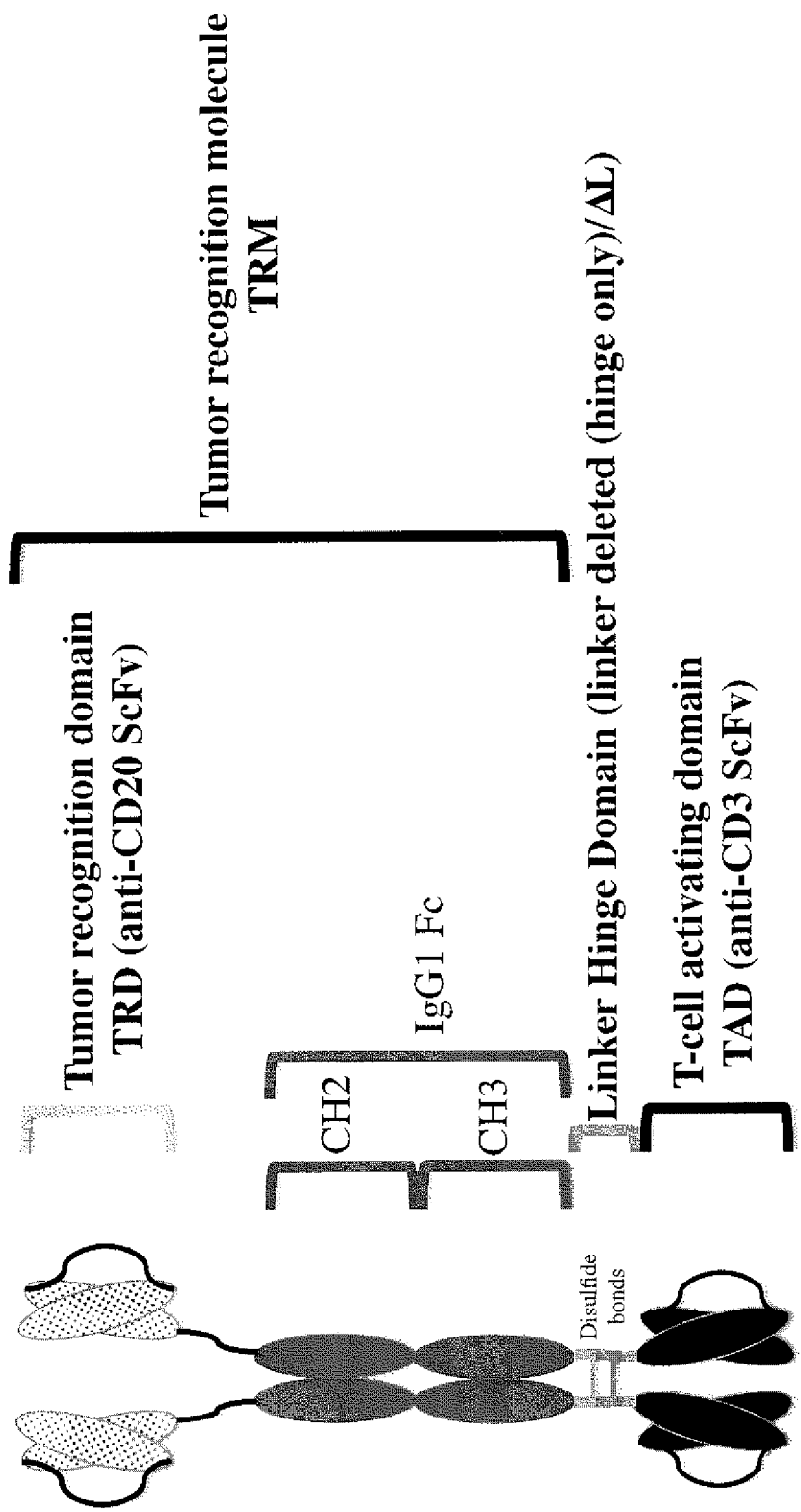

FIG. 1C illustrates a variant of the bispecific antibody (BsAb) shown in FIG. IA. They have the identical TRM and TAD. However, the LHD domain in this variant has the sequence of SEQ ID NO: 8 (Table 1), i.e., without the GGGGS linker sequence SEQ ID NO:9). This variant is referred to as ScFv-IgGΔL BsAb. Like the parental format, disulfide links within the LHD of ScFv-IgGΔL BsAb are generated following dimerization of monomeric ScFv-IgGΔL BsAb, as shown in FIG. 1C.

Figure 1D:
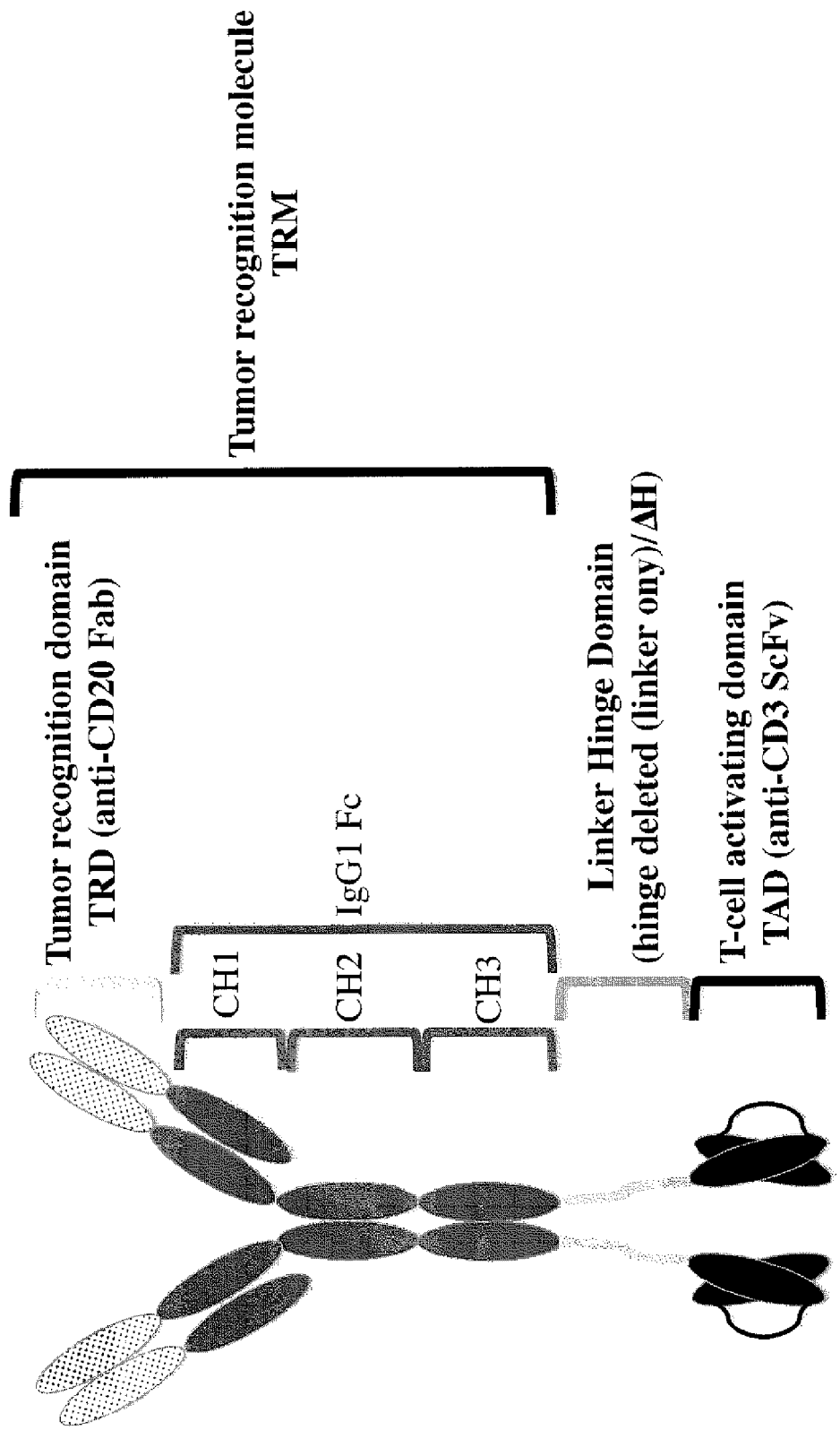

FIG. 1D shows another variant of the bispecific antibody shown in FIG. 1A. In this variant, the LHD has the sequence of SEQ ID NO: 7 (Table 1), which lacks the CPPCP hinge sequence (SEQ ID NO:8). This variant is referred to as IgG-FLΔH BsAb. Because the LHD lacks the cysteine residues for disulfide bond formation, IgG-FLΔH BsAb is free of disulfide linkage between the two LHDs.

Figure 1E:
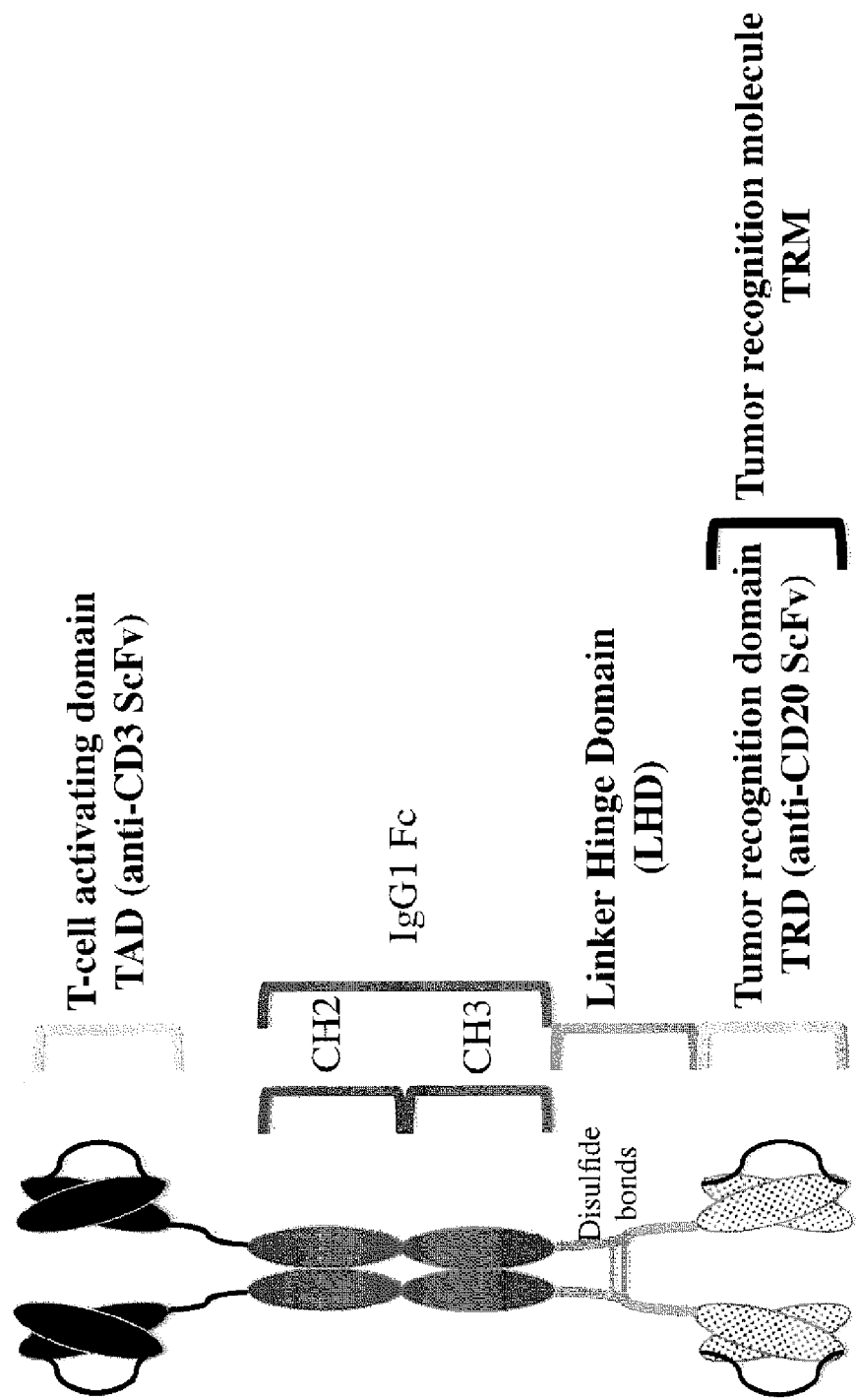

FIG. 1E shows an analog of the BsAb of FIG. 1A. In this analog, the TRD and TAD domains are swapped—i.e., the TAD is at the N-terminus of the IgG1 Fc, while the TRD is at the C-terminus of the LHD. This analog, referred to as "N-terminal TAD BsAb," has the identical bi-specificities as those of the BsAb shown in FIG. 1A.

The BsAbs described above have improved properties, such as production yields and stabilities, while at the same time retain their binding specificities and potencies, as illustrated below.

The BsAbs described above have improved properties production yields and stabilities, while at the same time retain their binding specificities and potencies, as illustrated below.

BsAb with LHD Delivered Improved Productions

Production plays a key role in commercialization of protein-based therapeutic agents. In accordance with embodiments of the invention, the inclusion of LHD in proteins could improve the yields of multi-specific molecules. To demonstrate the utility of LHD according to embodiments of the invention, ScFv-IgG, IgG-FL and IgG-FLΔH BsAbs were cloned, expressed, and tested on FS293 mammalian cells to evaluate their productions and stabilities.

Results from these tests showed that regardless the repeats of the linker sequence in the LHD, all BsAb formats share similar production rates (≥1 μg/ml) under transient transfection productions. Although IgG-FLΔH BsAb has a crude yield comparable to those of the IgG-FL or ScFv-IgG BsAb formats, a poor recovery rate was noticed for the IgG-FLΔH BsAb following purification (Table 2).

TABLE 2

The Recovery Rates of BsAb with LHD Constructs Following Purification

| SEQ ID NO | Label | Recovery Rates |
|---|---|---|
| 1 | 15H | ≥90% |
| 2 | 10H | ≥90% |
| 3 | 5H | ≥90% |
| 4 | 10H5 | ≥90% |
| 5 | 5H10 | ≥90% |
| 6 | 5H5 | ≥90% |
| 7 | ΔH | ≤45% |
| 8 | ΔL | ≥90% |

Figure 3:
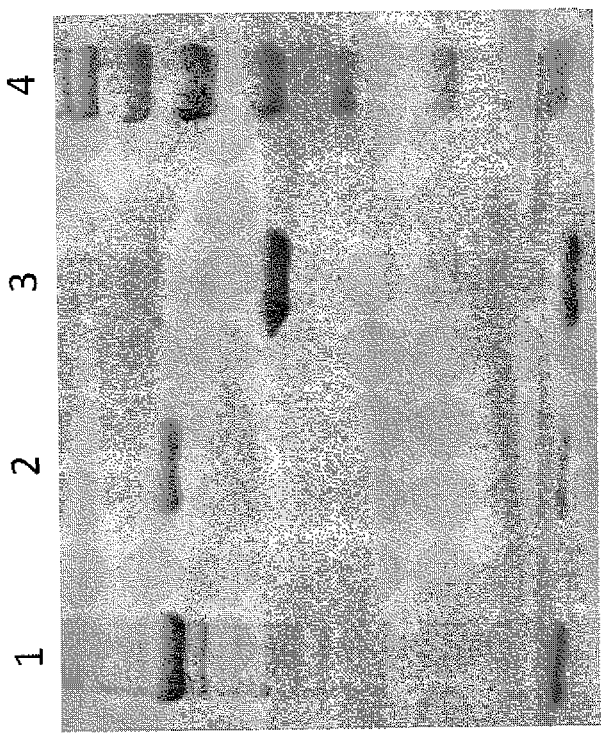
FIG. 3 shows stabilities of various BsAbs after long term storage.

Further analysis revealed that significant amounts of aggregate formation that was pelleted down at the bottom of purification apparatus for the IgG-FLΔH BsAb. Subsequent SDS analysis showed that BsAb was the major component of these pellets (FIG. 3).

Figure 4:
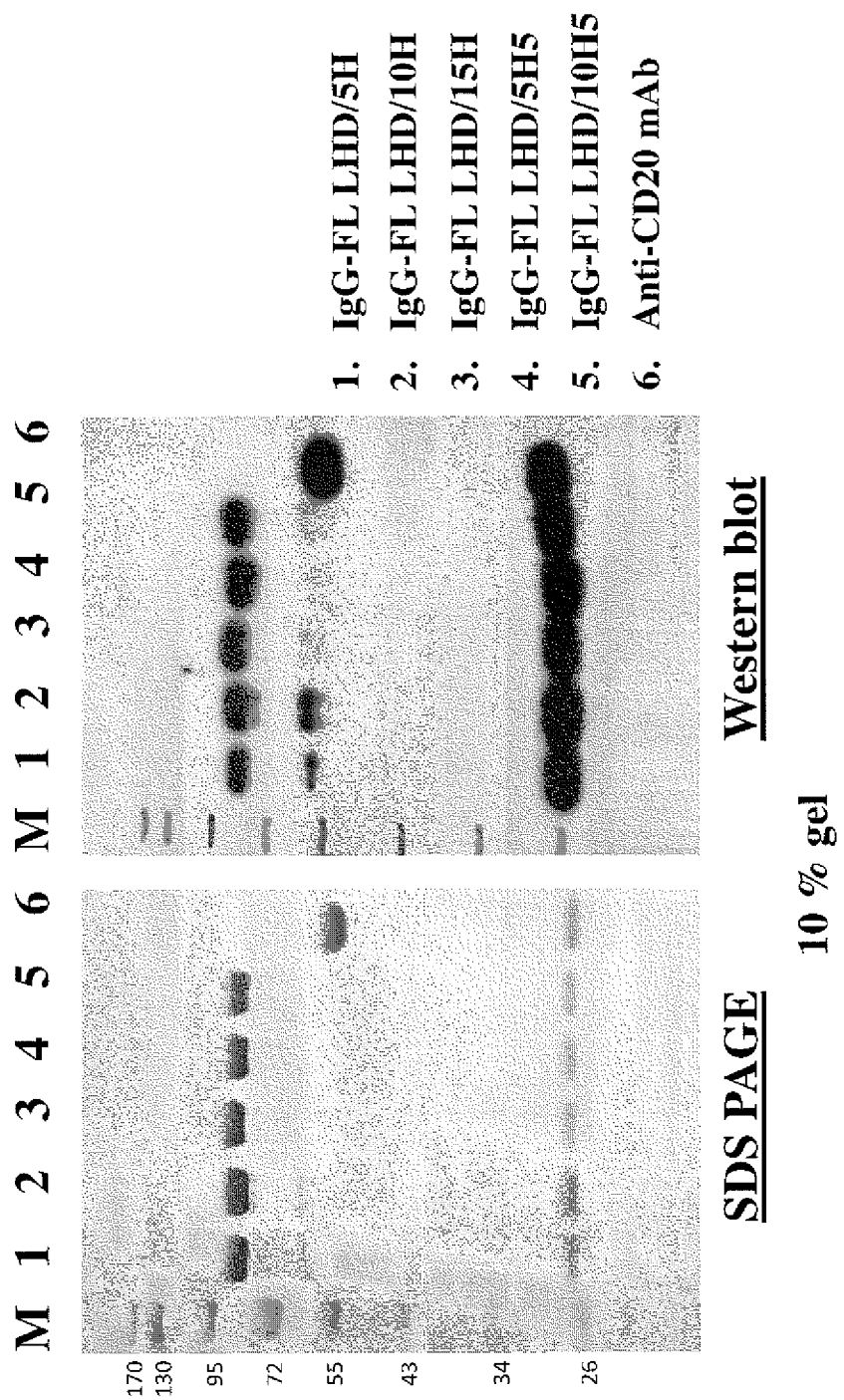
FIG. 4 shows binding affinities of a BsAb without a hinge in the LHD and BsAbs having various linker lengths in accordance with embodiments of the invention.

Stability of protein drugs at liquid storage under 4° C. has been an issue in protein engineering, particularly linker-containing proteins (see U.S. Patent Application Publication N. 2009/0175867 A1). The examples described herein showed that mild proteolytic cleavages were observed on BsAbs with one to two linker-repeats, but rarely on other LHD constructs (FIG. 4).

The Antigen-Binding Capability is not Compromised for BsAb with LHD

The binding to CD3 on T-cell surface is essential for BsAb to acquire T-cell mediated cytotoxicity. The CD3 molecule is a co-receptor of the T-cell receptor (TCR) and is responsible for the signaling following stimulations of the MHC and antigen complexes. Fusion of anti-CD3 ScFv directly to the C-terminus of ScFv-IgG, IgG-FL and IgG-FLΔH BsAbs produced some negative impacts to the CD3 binding capacities of these molecules, as shown in Table 3.

TABLE 3

Binding Constant Analysis of LHD Fusion BsAb to CD20 and CD3

| SEQ No. | Label | Binding to CD20 (IgG-FL BsAb) M | Binding to CD3 (IgG-FL BsAb) M |
|---|---|---|---|
| 1 | 15H | $2\text{-}4 \times 10^{-8}$ | $2.7 \times 10^{-8}$ |
| 2 | 10H | $2\text{-}4 \times 10^{-8}$ | $3.3 \times 10^{-7}$ |
| 3 | 5H | $2\text{-}4 \times 10^{-8}$ | $6 \times 10^{-8}$ |
| 4 | 10H5 | $2\text{-}4 \times 10^{-8}$ | $5.2 \times 10^{-8}$ |
| 5 | 5H10 | $2\text{-}4 \times 10^{-8}$ | — |
| 6 | 5H5 | $2\text{-}4 \times 10^{-8}$ | $1.5 \times 10^{-7}$ |
| 7 | ΔH | $2\text{-}4 \times 10^{-8}$ | — |
| 8 | ΔL | | |
| | Anti-CD3 mAb | — | $1 \times 10^{-9}$ |
| | ScFv-IgG (15H) | $8\text{-}9 \times 10^{-8}$ | $5 \times 10^{-8}$ |
| | Chemically Conjugated BsAb | $2\text{-}4 \times 10^{-8}$ | $1 \times 10^{-9}$ |

Figure 2A:
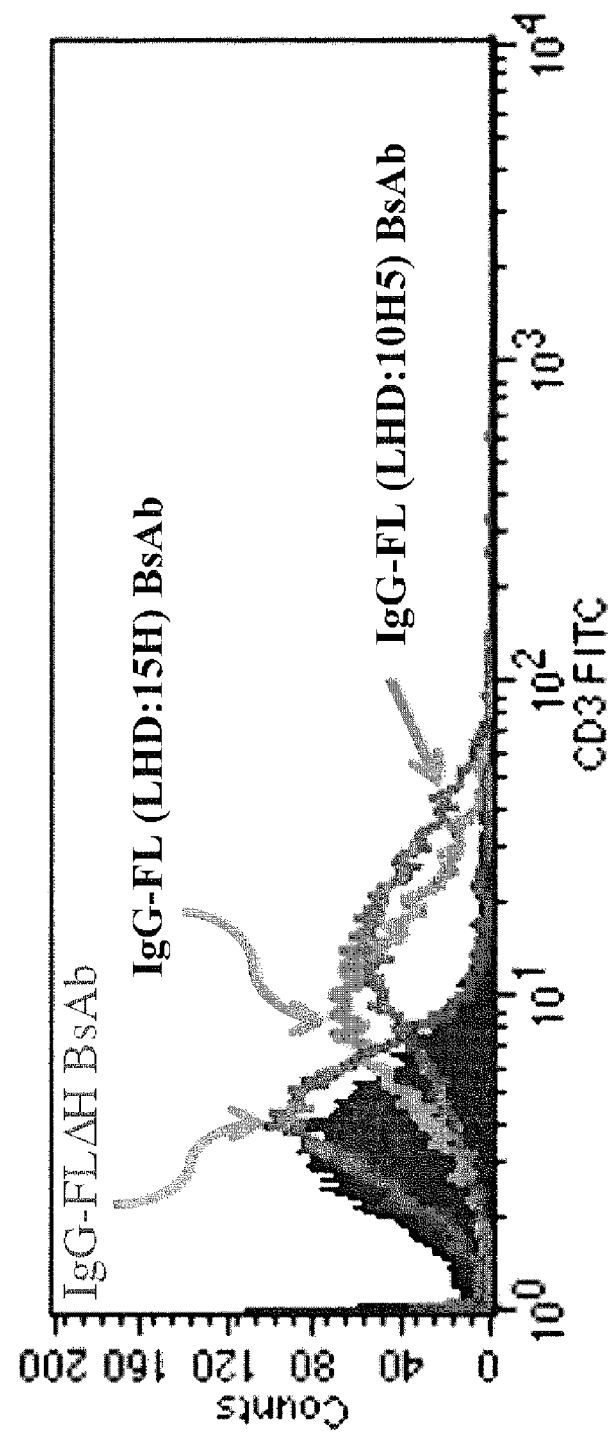
FIGS. 2A and 2B show results of electrophoresis, illustrating aggregation of IgG-FLΔH BsAb.
Figure 2B:
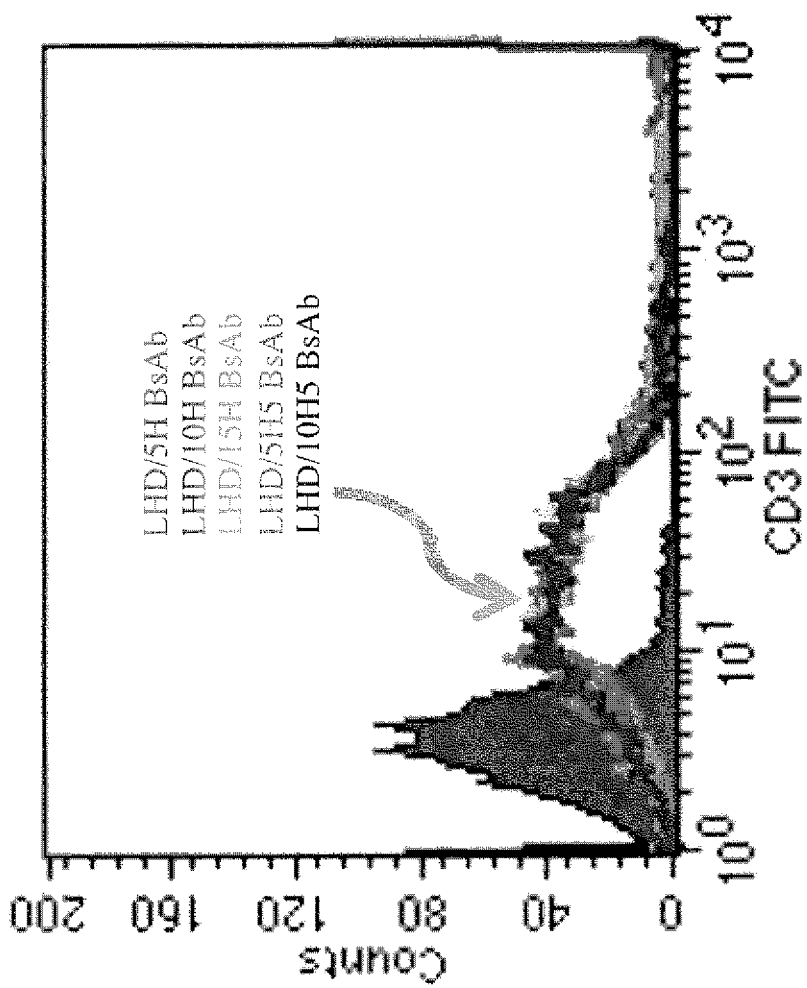

Among these BsAbs, IgG-FLΔH BsAb suffered the most significant reduction in CD3 binding (Table 3 and FIG. 2A). Such unpredicted outcome highlights the necessity of LHD for a biologically effective BsAb. However, changes in the length of linker sequences within LHD are insufficient to fully restoreCD3 bindings to BsAbs (Table 3). Compared to the parent, full-length anti-CD3 antibody, decreased affinities to the ligand (CD3) by both ScFv-IgG and IgG-FL BsAbs were observed (Table 3). On the other hand, the binding constants to CD20-expressing lymphoma by three BsAbs (ScFv-IgG, IgG-FL and IgG-FLΔH) were not affected (Table 3).

Figure 5A:
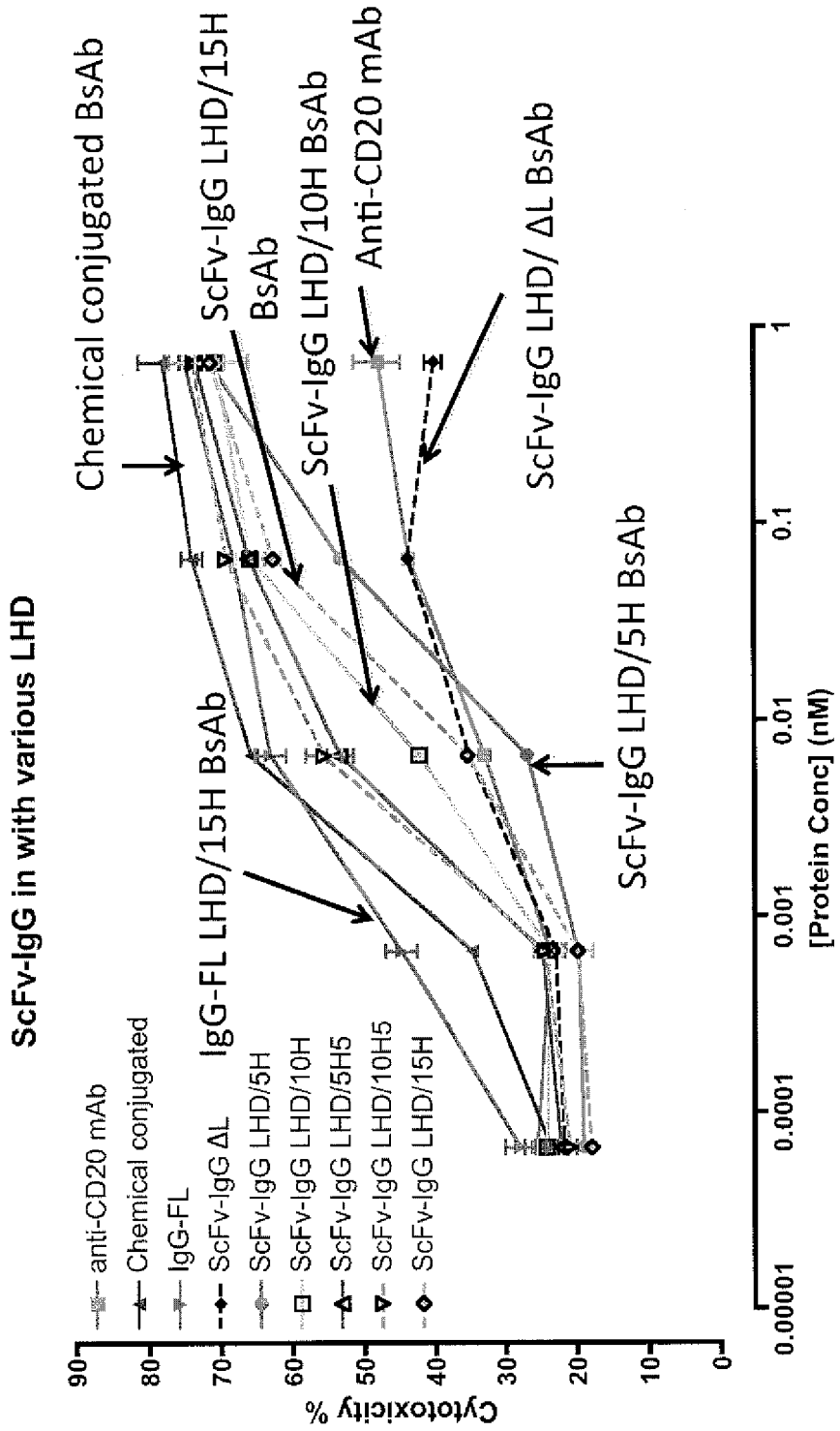
FIGS. 5A-5C show cytotoxicities of various BsAbs according to embodiments of the invention.

The T-cell mediated cytotoxicity against tumor is the Holy Grail of BsAb therapy. The following examples show that an LHD helps BsAbs to perform enhanced T-lymphocyte-mediated tumor-eradication. Like chemically conjugated BsAb, both IgG-FL and ScFv-IgG BsAbs were capable of eliminating CD20⁺B-cell lymphoma at low concentrations (FIG. 5A). Removing linker sequence (GGGGS; SEQ ID NO:9) from the LHD (i.e., ScFv-IgGΔL BsAb) also eliminates the T-lymphocyte mediated cytotoxicity (FIG. 5A).

Figure 5B:
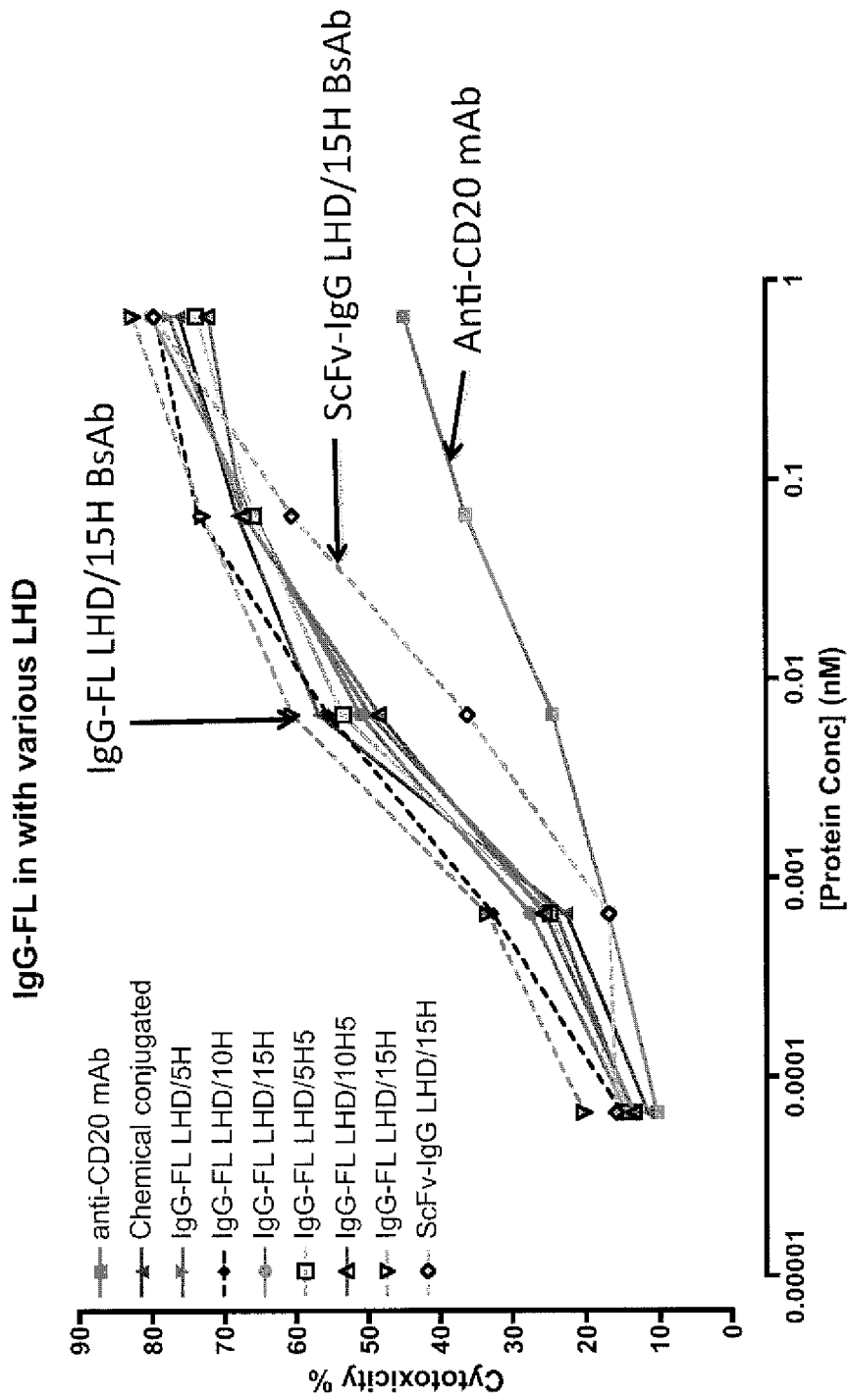
Figure 5C:
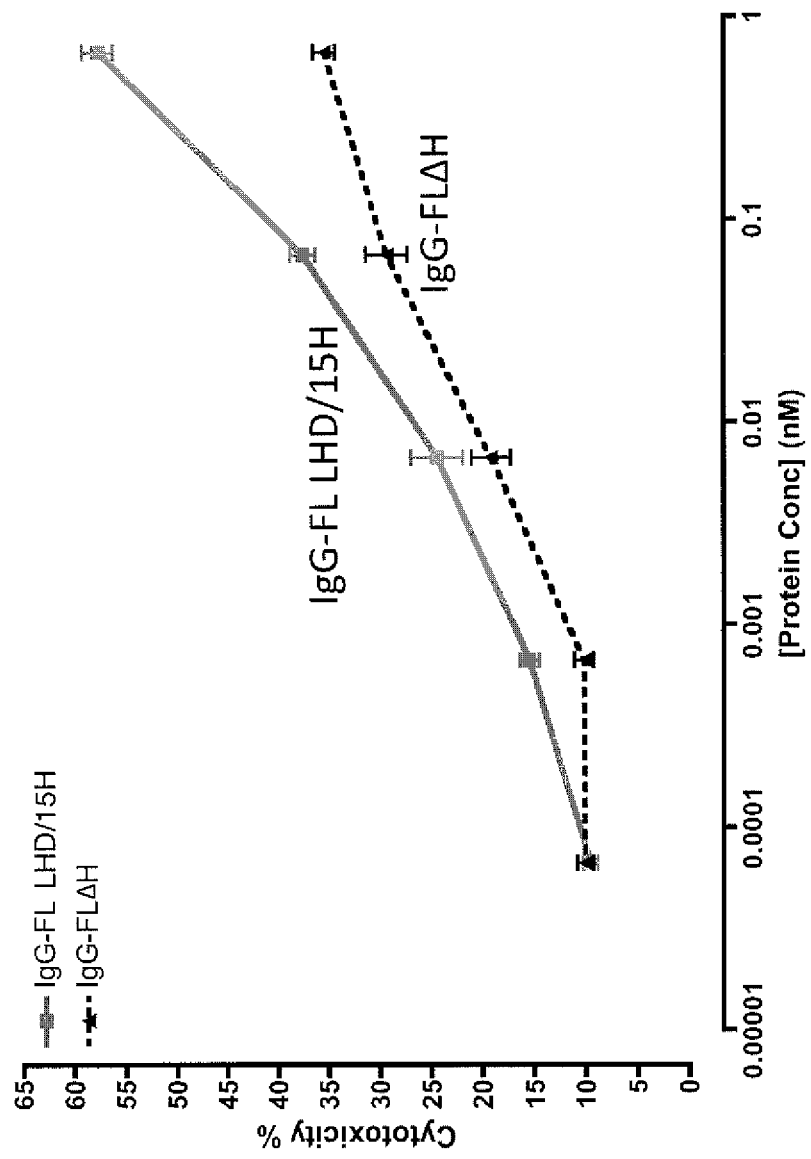

IgG-FLΔH BsAb shares high degree of structural similarity with IgG-FL BsAb, except that IgG-FLΔH BsAb lacks the CPPCP sequence (SEQ ID NO:8) and, therefore, cannot form LHD-associated disulfide linkages following dimerization. The lack of LHD-associated disulfide linkage resulted in significant reductions in T-lymphocyte mediated cytotoxicity (FIG. 5C).

Although, BsAb with an LHD between TRM and TAD delivered improved tumor-specific cytotoxicity, the level of improvement is not universal to the LHD sequences listed in Table 1. It was found that the optimal cytotoxicity for ScFv-IgG BsAb was associated to SEQ ID 4, 5 or 6 (Table 1, FIG. 5A). Such variations in tumor-specific cytotoxicity, however, became indistinguishable when full set of anti-CD20 mAb was used as TRM in IgG-FL format (FIG. 5B). Rituxan®, an anti-CD20 mAb has been shown to mediate B-cell depletion via antibody dependent cell mediated cytotoxicity (ADCC). Our experiments demonstrated that LHD comprised BsAbs, such as IgG-FL and ScFv-IgG formats, are more efficient in eradicating B-lymphoma via ADCC than Rituxan® (FIGS. 5A, 5B and Table 4). Prior results showed that Rituxan®-induced ADCC requires a higher effecter:target ratio (E:T ratio, 40:1 or higher) and higher Rituxan® titer (μg/ml) to keep maximal cytotoxicity at 30-50%. The IgG-FL BsAb format of selected LHD, however, delivered not only improved tumor eradication capability (up to 80%), but also reduce the E:T ratio to 10:1 (Table 4).

TABLE 4

LHD Fusion BsAb Mediate Cytotoxicity Against Tumor Cells

| | | Cytotoxicity (BsAb) | | |
|---|---|---|---|---|
| | | ScFv-IgG with LHD BsAb Construct; E:T = 10:1 | | IgG-FL with LHD BsAb Construct; E:T = 10:1 |
| SEQ No. | Label | EC50 (pM) | Fold of Maximal Cytotoxicity Improved vs. anti-CD20 mAb | EC50 (pM) | Fold of Maximal Cytotoxicity Improved vs. anti-CD20 mAb |
| 1 | 15H | 14.2 | 2.55 | 4.0 | 2.78 |
| 2 | 10H | 9.5 | 2.55 | 2.0 | 2.82 |
| 3 | 5H | 41.7 | 2.55 | 4.6 | 2.82 |
| 4 | 10H5 | 3.9 | 2.55 | 3.5 | 2.82 |
| 5 | 5H10 | | | | |
| 6 | 5H5 | 4.3 | 2.55 | 2.8 | 2.82 |
| 7 | ΔH | | | 15.6 | 1 |
| 8 | ΔL | | ≤1 | | |

Figure 6:
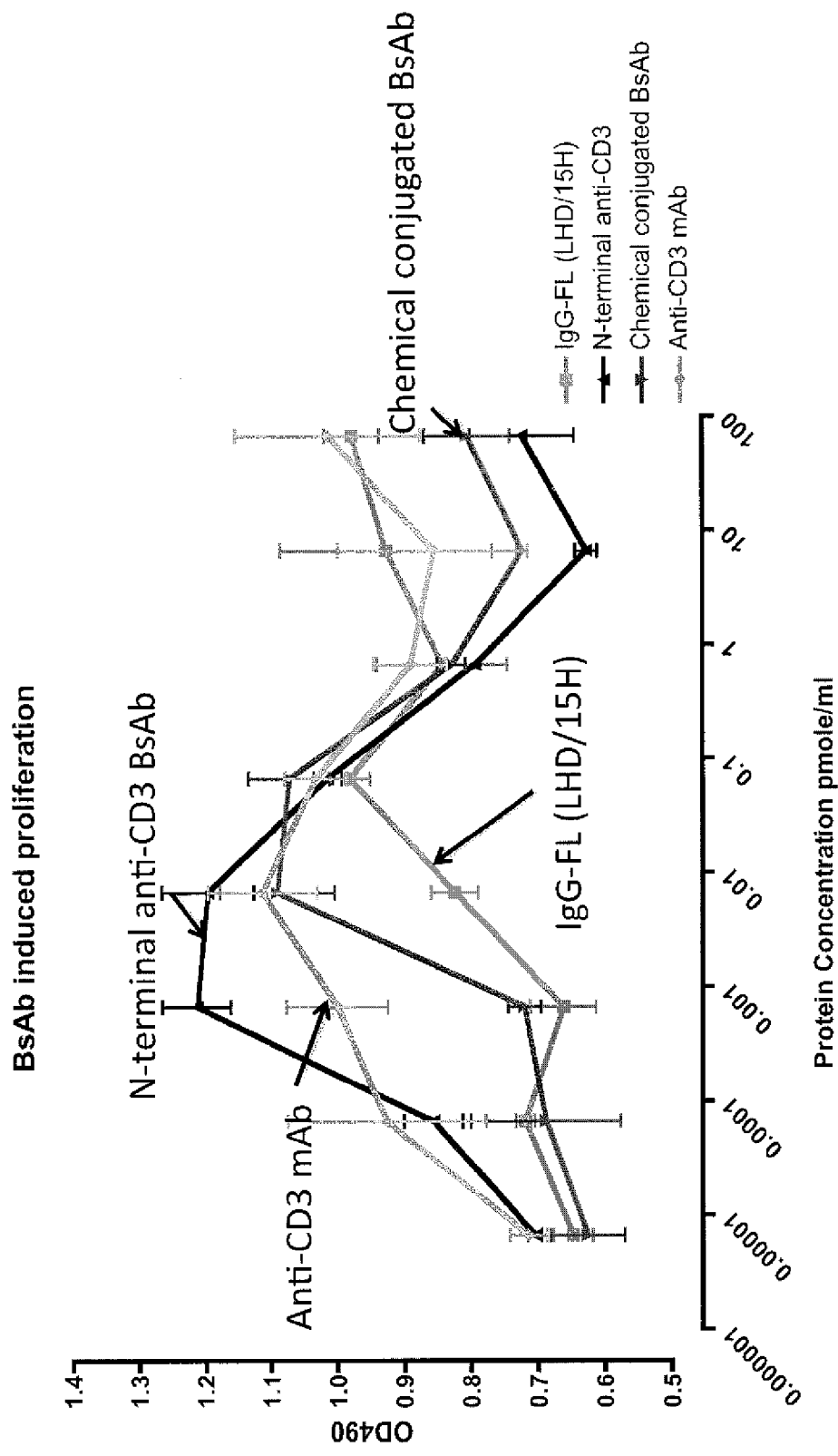
FIG. 6 shows BsAbs induce PBMC proliferation in accordance with embodiments of the invention.

ScFv-IgG BsAb with LHD and IgG-FL BsAb With LHD Induced Mild Proliferation on PBMC, as Compared to Parent Anti-CD3 Monoclonal Antibody The full-length monoclonal anti-CD3 antibody is a well-known mitogenic inducer for non-specific T-cell activation. It has been proposed that this mitogenicity is a major contributor to the adverse effects, such as flu-like symptoms and cytokine release syndrome (CRS), following monoclonal anti-CD3 antibody therapy. We showed that parent anti-CD3 mAb induces significant proliferation on freshly-cultured peripheral blood mononuclear cells (PBMC) (FIG. 6), same as N-terminal TAD BsAb (FIG. 1E). BsAb prepared by chemical conjugation of anti-CD20 mAb and anti-CD3 mAb showed a slightly decreased mitogenic potential, as compared to anti-CD3 mAb alone. IgG-FL/15H BsAb, however, only exhibited mitogenic effects at high concentrations (FIG. 6).

T-Cell Activation Markers were Enhanced by BsAb with LHD

The proliferation assay is a "standard" in measuring the activation of T-lymphocytes, regardless of the heterogeneous cellular outcomes following activation. We showed that IgG-FL BsAbs deliver enhanced cytotoxic effects to B-lymphoma, regardless of its reduced proliferation profile (FIGS. 5 and 6). To rationalize such observations, T-lymphocyte activation markers, both CD69 and CD25, were stained and revealed by FACS following various stimulations (Table 5). The examples showed that LHD-containing IgG-FL BsAb is more effective than anti-CD3 mAb in enhancing the expression of both CD69 and CD25. N-terminal TAD BsAb also share activation profiles similar to those of the LHD-containing IgG-FL BsAb. ScFv-IgG fused with LHD/ΔL is ineffective in tumor cell eradication (FIG. 5A), such loss in biological function is also reflected by loss of the capability in activating T-lymphocytes (Table 5).

TABLE 5

IgG-FL BsAb with LHD Enhances the Expression of CD69 and CD25

| | | Mean Fluorescence Index (MFI) | | |
|---|---|---|---|---|
| | | α-CD3 | α-CD69 | α-CD25 |
| Day 0 | Blank | 189.62 | 10.16 | 22.2 |
| Day 4 | Blank | 223.62 | 21.75 | 44.01 |
| | IL-2 | 240.74 | 148.76 | 108.7 |
| | Anti-CD3 mAb | 214.22 | 45.53 | 612.89 |
| | IgG-FL (LHD/15H) BsAb | 310.45 | 48.92 | 828.58 |
| | N-terminal Anti-CD3 BsAb | 314.97 | 49.09 | 697.62 |
| | Chemically Conjugated BsAb | 308.12 | 40.39 | 716.17 |
| | ScFv-IgG-LHD/ΔL BsAb | 244.09 | 23.35 | 51.86 |

Such results further indicate that the requirement of both linker and hinge for a functional LHD domain. These examples demonstrated that the inventive LHDs (Table 1) can maintain the biological activities of the linked molecules/domains and modulate the desirable biological characteristics.

IgG-FL BsAb with LHD Showed Improved Pharmacokinetic Property

The PK (pharmacokinetics) is an essential indicator for a successful drug because extended PK not only translates into a better stability, but also a less frequent dosing and better acceptance to patients and clinicians. The PK of IgG-FL on mice showed a $T^{1/2}$ of almost 96 hours (FIG. 7).

Constructing Bispecific Antibodies

Restriction enzymes were purchased from various venders, DNA polymerase, T4 DNA ligase Klenow enzyme and T4 DNA polymerase were from Invitrogen (Grand Island, N.Y.). All enzymes were used as recommended by the manufactures.

All primers for PCR amplifications were purchased from various venders. DNA amplifications were performed in a PCR machine from manufacturer using a predenaturing step, followed by pre-determined cycles, containing a denaturing step, an annealing step, and an extension step, each for 30 minutes.

All expression modules are schematically represented in FIGS. 1A-1E.

The anti-CD20 light chain and truncated heavy chain were cloned into vector vector A and vector B. A single-chain fragment of anti-CD20 VH and VL was cloned into vector C and used for subsequent anti-CD20 ScFv.

Cell Lines Preparation

The Raji cell used in this invention is a B-lymphoma tumor cell line obtained from Biorescouce Collection and Research Center (BCRC), which is a division of Food Industry Research and Development Institute (FIRDI) in Taiwan, R.O.C. The Jurkat cell is a T-lymphoma cell line from ATCC. Both Raji and Jurkat cells are cultured in RPMI 1640 medium (GibcoBRL Life Technologies, Paisly, UK) supplemented with 10% Fetal bovine serum (Hyclone), 0.03% L-glutamine and 0.4 mM of sodium pyruvate. After incubation at 37° C. humidified incubator containing 5% of $CO_2$, cells were sub-cultured or washed in sterilized buffer for testing.

Preparation of Peripheral Blood Mononuclear Cells (PBMC)

Peripheral blood mononuclear cells (PBMC) were isolated from whole blood of normal healthy adult donors with Ficoll-Paque PLUS by density centrifugation. Following the isolation, PBMC were cultured and activated for 6-14 days in RPMI-1640 medium supplemented with 10 ng/ml of anti-CD3 mAb, 75 IU/ml of interlekine-2 (IL-2) and 10% FBS.

Cytotoxicity Assays (Calcein AM Cytotoxicity)

The target cells (Raji) were labeled with 10 µM of Calcein for 30 min at 37° C. in phenol red free RPMI 1640 medium supplemented with 5% FBS. At the end of Calcein incubation, cells were washed twice with phenol red free RPMI 1640 medium with 5% FBS and the cell density was adjusted to $3 \times 10^5$ cells/ml with phenol red free RPMI 1640 with 5% FBS. For the reaction mixture, 100 µl of medium containing $3 \times 10^4$ cell were placed in each well of a 96-well culture plate. The cell density of effecter cells (PBMC) culture was calculated and adjusted to $3 \times 10^6$ cells/ml by phenol red free RPMI 1640 medium with 5% of FBS. For cytotoxic reactions, different quantities of different BsAb and 100 µl ($3 \times 10^5$ cells) of effecter cells were added into Raji preload, 96 well culture plate and incubated in 37° C., 5% $CO_2$ enriched incubator for 4 hours. At the end of the incubation, culture plate was centrifuged at 700 g for 5 minutes, then 130 µl of supernatant from each reaction well was transferred, individually, to a new plate and the dye released was quantitated in Fusion alpha micro-plate reader. The percent of cytotoxicity was calculated according to the formula:

[fluorescence(sample)−fluorescence(control)]/[fluorescence(total-lysis)−fluorescence(control)]*100.

The total-lysis was defined as target cells treated with 0.9% of Triton for 10 minutes.

Flow Cytometry Assays

Biding Affinity to Tumor Target (B-Lymphoma)

Raji cells ($1 \times 10^6$ cells/reaction) were treated with different BsAbs at different concentrations at room temperature for 30 minutes. At the end of the incubation, all reactions were washed twice with PBS supplemented with 2% of FBS. After wash, cells were re-incubated with 1 µl of FITC conjugated, affinity purified F(ab')2 fragment, goat anti-human IgG (Fab')2 fragment-specific antibody for 30 minutes at room temperature. Following the incubation, cells were washed twice with ice cold PBS supplemented with 2% FBS and monitored by FACS apparatus.

Jurkat cells ($1 \times 10^6$ cells/reaction) were treated with different BsAbs at different concentrations at room temperature for 30 minutes. At the end of the incubation, all reactions were washed twice with PBS supplemented with 2% of FBS. After wash, cells were re-incubated with 1 µl of FITC conjugated, affinity purified F(ab')2 fragment, goat anti-human IgG (Fab')2 fragment-specific antibody for 30 minutes at room temperature. Following the incubation, cells were washed twice with ice cold PBS supplemented with 2% FBS and monitored by FACS apparatus.

The T-Lymphocyte Activation Markers Analysis

Peripheral blood mononuclear cells (PBMC) were isolated as described in the "Preparation of peripheral blood mononuclear cells (PBMC)" section, except that the isolated PMBC were activated for 2 or 4 days. The immune fluorescence staining of PMBC with anti-human CD25 and CD69 markers was performed as described in the "Biding affinity to tumor target" section, except that the target cells used were activated PBMC. Briefly, $1 \times 10^6$ cells/reaction were treated with either fluorescent conjugated anti-human CD25 or CD69 monoclonal antibodies at different concentrations at room temperature for 30 minutes. At the end of the incubation, all reactions were washed twice with PBS supplemented with 2% of FBS. After wash, cells were monitored by FACS apparatus.

The PK Analysis on Fusion Proteins Comprising LHD Fused Bispecific Antibody

Balb/c mice (n=4) were injected with 3 mg/kg of anti-CD20 IgG-LHD-anti-CD3/ScFcBsAb and blood samples were collected at various time points. Sera from collected animals were collected via centrifugation and the concentrations of BsAb were measured via ELISA. Briefly, serial diluted mouse sera were incubated in ELISA plate precoated with anti-human Fab antibody (Jackson Lab) for an hour. Following the incubation, microtiter plates were washed with PBST buffer several times and blocked by 5% skim milk for an hour. At the end of blocking, microtiter plates were wash again by PBST and re-incubated with HRP conjugated anti-human Fc antibody for an hour. Following this incubation, microtiter plates were washed again and color was developed and detected as manufacture suggested.

While bispecific biomolecules are illustrated, one skilled in the art would appreciate that multi-specific biomolecules may also be prepared with this approach. Similarly, the linker sequence is illustrated using GGGGS (SEQ ID NO:9) and the hinge sequence is illustrates using CPPCP (SEQ ID NO:8). However, one skilled in the art would appreciate that other similar sequences may be used. The linker sequence is to provide a proper spacing for the different domains, while the hinge domain is to provide residues for disulfide linkage formation in homodimers.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A biomolecule comprising two bispecific proteins, wherein each of the bispecific protein comprises a protein domain, an N-terminal moiety fused to the N-terminus of the protein domain via a peptide bond and a C-terminal moiety fused to the C-terminus of the protein domain via a peptide bond, the protein domain being a linker hinge domain (LHD) comprising a linker sequence directly linked, via a peptide bond, to a hinge sequence to form a contiguous protein domain, wherein the linker sequence comprises glycine-glycine-glycine-glycine-serine (SEQ ID NO: 9), and the hinge sequence comprises cysteine-proline-proline-cysteine-proline (SEQ ID NO: 8),
   wherein the two bispecific proteins are linked to each other via one or more disulfide bonds between the hinge sequences of the two bispecific proteins, and
   wherein, in each of the two bispecific proteins, the N-terminal moiety and the C-terminal moiety are each independently a full-length immunoglobulin or a single-chain variable region fragment (ScFv) of an antibody.

2. The biomolecule of claim 1, wherein, in each of the two bispecific proteins, one of the N-terminal moiety and the C-terminal moiety comprises a moiety selected from the group consisting of a T-lymphocyte activating domain that comprises an anti-CD3 antibody and a single-chain variable region fragment (ScFv) of the anti-CD3 antibody, and wherein the other of the N-terminal moiety and the C-terminal moiety comprises a moiety selected from the group consisting of a tumor recognition domain that comprises an anti-CD20 antibody and a single-chain variable region fragment (ScFv) of the anti-CD20 antibody.

3. The biomolecule of claim 1, wherein, in each of the two bispecific proteins, the N-terminal moiety comprises an anti-tumor specific marker, an inflammatory disease marker, an autoimmune disease marker, or an allergy-related marker.

4. The biomolecule of claim 2, wherein, in each of the two bispecific proteins, the C-terminal moiety comprises the anti-CD3 antibody, and the N-terminal moiety comprises the anti-CD20 antibody.

5. The biomolecule of claim 1, wherein the biomolecule maintains solubility during expression, production or purification.

6. The biomolecule of claim 1, wherein the biomolecule has a mitogenicity lower than a mitogenicity of an anti-CD3 monoclonal antibody.

7. The biomolecule of claim 1, wherein the biomolecule has an ability to induce CD69 and CD25 expression at a level no less than a level induced by an anti-CD3 monoclonal antibody.

8. The biomolecule of claim 1, wherein, in each of the two bispecific proteins, the protein domain comprises the sequence of SEQ ID NO: 1, SEQ ID NO: 2, SEQ ID NO: 3, SEQ ID NO: 4, SEQ ID NO: 5, or SEQ ID NO: 6.

9. The biomolecule of claim 2, wherein, in each of the two bispecific proteins, the protein domain comprises the sequence of SEQ ID NO: 1, SEQ ID NO: 2, SEQ ID NO: 3, SEQ ID NO: 4, SEQ ID NO: 5, or SEQ ID NO: 6.

10. The biomolecule of claim 3, wherein, in each of the two bispecific proteins, the protein domain comprises the sequence of SEQ ID NO: 1, SEQ ID NO: 2, SEQ ID NO: 3, SEQ ID NO: 4, SEQ ID NO: 5, or SEQ ID NO: 6.

11. The biomolecule of claim 4, wherein, in each of the two bispecific proteins, the protein domain comprises the sequence of SEQ ID NO: 1, SEQ ID NO: 2, SEQ ID NO: 3, SEQ ID NO: 4, SEQ ID NO: 5, or SEQ ID NO: 6.

12. The biomolecule of claim 5, wherein, in each of the two bispecific proteins, the protein domain comprises the sequence of SEQ ID NO: 1, SEQ ID NO: 2, SEQ ID NO: 3, SEQ ID NO: 4, SEQ ID NO: 5, or SEQ ID NO: 6.

13. The biomolecule of claim 6, wherein, in each of the two bispecific proteins, the protein domain comprises the sequence of SEQ ID NO: 1, SEQ ID NO: 2, SEQ ID NO: 3, SEQ ID NO: 4, SEQ ID NO: 5, or SEQ ID NO: 6.

14. The biomolecule of claim 7, wherein, in each of the two bispecific proteins, the protein domain comprises the sequence of SEQ ID NO: 1, SEQ ID NO: 2, SEQ ID NO: 3, SEQ ID NO: 4, SEQ ID NO: 5, or SEQ ID NO: 6.

* * * * *